METHOD FOR THE PREPARATION OF A BIOCIDAL FORMULATION CONTAINING STARCH AND *BACILLUS THURINGIENSIS*

United States Patent [19]
Yang et al.
[11] Patent Number: 5,352,597
[45] Date of Patent: Oct. 4, 1994
[54] **METHOD FOR THE PREPARATION OF A BIOCIDAL FORMULATION CONTAINING STARCH AND *BACILLUS THURIN

FIELD OF THE INVENTION

This invention relates to a method for the preparation of biocidal formulations. More particularly, this invention relates to an improved method for the preparation of effective biocidal formulations that does not require the addition of large amounts of water during the preparation steps thus allowing the process time to be substantially shortened.

BACKGROUND OF THIS INVENTION

The invention relates to the preparation of biocidal formulations. Conventionally, the extermination of agricultural pests always involves the application of large amounts of chemical pesticides. It is well-known that chemical pesticides may cause pests to develop resistance to pesticides, and that residuals of pesticides often cause pesticidal pollution to the environment. Since chemical pesticides have potential danger to human beings (and animals) and the environment, the use of chemical pesticides should be judiciously controlled and the amount of usage maintained to a minimum. It is preferred to develop biocides which can selectively and effectively kill pests while they can be degraded in the environment. It is also highly preferable to develop biocides that will not cause harms to human beings and the crops.

One of the main disadvantages of biocides is that they cannot resist high temperature. If the preparation of biocidal formulations is conducted at elevated temperatures, the biocides may be destroyed or their activities substantially reduced. Therefore, conventionally, the preparation of biocidal formulation must be processed at low temperatures in order to protect biocides and to maintain the activity thereof.

R. L. Dunkle et at. disclose a method for the preparation of starch-encapsulated *Bacillus thuringiensis* in "Environmental Entomology" (vol. 17, PP. 120–126, 1988). In this reference, the method for the preparation of starch-encapsulated biocide is described as follows. Refined corn oil (2 g) was mixed with pre-gelatinized starch powder (25 g). Chilled distilled water (60 ml, 2° C.) containing a suspension of *Bacillus thuringiensis* spores and crystals at a desired concentration was stirred into the starch-oil mixture to form a gelatinous mass. The mixture was allowed to stand for 30 minutes at room temperature to produce a rubbery, non-sticky mass which was processed in a blender with 25 g of starch powder to produce pesticide-containing small particles. After air dried for 24 hours at room temperature, the particles were sieved into various mesh sizes. This process, which involved cooling at room temperature for 24 hours, was employed in order to avoid the reduction of the activity of biocide due to heat or high temperature. This process is cumbersome and cannot be performed as a continuous process.

SUMMARY OF THE INVENTION

The primary object of the present invention is to develop a method for the preparation of effective biocidal formulations which requires relatively short processing time and thus provides the benefits of low production cost and reduced exposure to the pesticides by the operators thus reducing health risks. More particularly, the primary object of the present invention is to develop an improved and more efficient method for the preparation of effective biocidal formulations by which the ingredients of the biocidal formulation are processed at high temperature while the activity of the biocide is maintained.

In the process disclosed in the present invention, pre-gelatinized starch, natural starch, biocide, water and, optionally, protective agent or agents, are blended together to form a mass. The mass is pressed and dried by a hot roller to form a flake. Subsequently, the flake is crushed to form the final product. In the process disclosed in the present invention, it does not employ large amounts of water and does not require a long period of process time in order to dry the final product. Furthermore, in the process disclosed in the present invention, biocide formulations can be prepared at elevated temperatures in a continuous manner. Therefore, the present invention allows substantial economic advantages to be realized relative to the prior art processes in the preparation of biocidal formulations. The present invention also reduces the potential health risks to which an operator may be exposed during the preparation of biocidal formulations as a result of the substantial reduction of process time.

Drying takes no more than 30 minutes, preferably between 3 and 15 minutes, at between 50° and 100° C.

DESCRIPTION OF THE PREFERRED EMBODIMENT

The present invention will now be described more specifically with reference to the following examples. It is to be noted that the following descriptions of examples including preferred embodiments of this invention are presented herein for purpose of illustration and description; it is not intended to be exhaustive or to limit the invention to the precise form disclosed.

PREPARATION OF THE CULTURE OF *Bacillus thuringiensis*

*Bacillus thuringiensis* was added into a 500 ml Hinton flask which contained 75 ml of an appropriate culture medium. The flask was stirred at 200 rpm and 30° C. for 72 hours. The flask was sampled and was found to contain $2-3 \times 10^9$ spores/ml. The spores were freeze-dried.

EXAMPLE 1

The spores of *Bacillus thuringiensis* were heated at 60°–100° C. for 3 minutes and 15 minutes respectively, and their ability to kill 3-instar moth larva as well as their ability to survive elevated temperatures were tested. The test results are shown in Table 1.

TABLE 1

| Temperature (°C.) | Time (minutes) | Mortality of moth larva (%) | | |
|---|---|---|---|---|
| | | 1 day | 2 days | 3 days |
| 100 | 3 | 0 | 78 | 100 |
| 90 | 3 | 0 | 92 | 98 |
| 90 | 15 | 25 | 98 | 100 |
| 80 | 3 | 3 | 100 | 100 |
| 80 | 15 | 43 | 96 | 100 |
| 70 | 3 | 11 | 100 | 100 |
| 70 | 15 | 35 | 98 | 100 |
| 60 | 3 | 4 | 98 | 100 |
| 60 | 15 | 62 | 98 | 100 |
| without heating | 0 | 34 | 97 | 98 |

As shown in Table 1, the activity of *Bacillus thuringiensis* was maintained after being subject to the condition of 90° C. for 15 minutes. Therefore, the preparation of *Bacillus thuringiensis* biocidal formulation below 90° C. for no more than 15 minutes will maintain the activity of *Bacillus thuringiensis*.

EXAMPLE 2

Pre-gelatinized starch (50 g), natural starch (50 g), corn oil (2 g), *Bacillus thuringiensis* (0.5 g) and water (22.5 g) were blended to form a mass. The total amount of water was only 22.5% of the total amount of starch. Since the amount of water is small, the mass was easily dried and crushed into flakes.

EXAMPLE 3

Pre-gelatinized starch (16.25 g), natural starch (81.3 g), *Bacillus thuringiensis* (0.5 g), and water (53.6 g) were blended to form a homogeneous mass. The total among of water was 55% of the total amount of starch. The mass was dried and crushed into flakes and dried at room temperature. The particle size of final product was measured to be less than 900μ. The product contained 0.5% of *Bacillus thuringiensis*. The ability of the final product to kill 100 pieces of 3-instar moth larva was tested with the test results summarized in Table 2. As it can be seen in Table 2, the blends of *Bacillus thuringiensis* with starch did not affect the biocidal function of *Bacillus thuringiensis*.

TABLE 2

|  | Mortality of moth larva (%) | | |
| --- | --- | --- | --- |
|  | 1 day | 2 days | 3 days |
| Starch/*Bacillus thuringiensis* formulation | | | |
| 0.5 g/30 g culture medium | 2 | 26 | 62 |
| 1 g/30 g culture medium | 2 | 43 | 96 |
| 2 g/30 g culture medium | 0 | 56 | 100 |
| *Bacillus thuringiensis* formulation | | | |
| 0.0025 g/30 g culture medium | 0 | 35 | 88 |
| 0.005 g/30 g culture medium | 4 | 45 | 88 |
| 0.01 g/30 g culture medium | 0 | 62 | 96 |

EXAMPLE 4

Pre-gelatinized starch (16.25 g), natural starch (81.3 g), *Bacillus thuringiensis* (2 g), and water (53.6 g) were blended to form a mass. The mass was rolled and pressed using a hot roller at 60°–90° C. for 2–5 minutes. The later step caused the mass to be dried. The mass was then crushed to obtain starch-encapsulated *Bacillus thuringiensis* formulation. 0.32 g of the *Bacillus thuringiensis* formulation was dispersed in 10 c.c water. 2 c.c. of the aqueous solution was sprayed onto the leaves of a cabbage (the diameter of the leaves was about 4.2 cm), with 1 c.c. of the aqueous solution sprayed on each side of the leaf. 3-instar moth larva were planted on the leaves to test the mortality thereof in the present of the aqueous biocidal formulation. A comparative experiment was conducted which did not contain starch. In the comparative study, *Bacillus thuringiensis* (0.064 g) was dispersed in water (100 c.c.) 2 c.c. of the solution was sprayed on the cabbage leaves to test the mortality of moth larva.

The results are shown in Table 3. In Table 3, it is shown that the starch-encapsulated *Bacillus thuringiensis* which was treated at 60°–90° C. for 2–5 minutes was able to retain all its activity.

TABLE 3

| Temperature (°C.) | Time (minutes) | Mortality of moth larva (%) | | |
| --- | --- | --- | --- | --- |
|  |  | 1 day | 2 days | 3 days |
| 60 | 5 | 0 | 100 | 100 |
| 70 | 4 | 0 | 100 | 100 |
| 80 | 3.5 | 0 | 93 | 100 |
| 90 | 2.5 | 0 | 100 | 100 |
| Comparative Experiment |  | 0 | 15 | 100 | 100 |

Table 4 provides a comparison between the process disclosed in the present invention and that in the cited reference of Dunkle et at. As shown in Table 4, the amount of water used in preparation the biocidal formulation of the present invention is 22.5~55%. On comparison, the amount of water used in the cited reference is 120%. Most importantly, with the process disclosed in the present invention, the amount of process time was reduced from 24 hours of the cited reference to about 2 to 15 minutes of the present invention. Thus substantial economic benefits can be obtained by the present invention.

TABLE 4

|  | This invention | Prior Art Method |
| --- | --- | --- |
| total amount of starch (weight basis) | 1.0 | 1.0 |
| pre-gelatinized starch | 0.16 ~ 0.40 | 0.50 |
| natural starch | 0.84 ~ 0.60 | 0.50 |
| amount of water (weight basis) | 0.225 ~ 0.55 | 1.20 |
| process temperature | 60 ~ 90° C. | room temperature |
| process time | 2 ~ 15 minutes | 24 hours |

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A method for the preparation of a biocidal formulation comprising the steps of:
    (a) blending predetermined amounts of pre-gelatinized starch, unpre-gelatinized starch, biocide and water to form a mass, wherein the ratio between the unpre-gelatinized starch and the pre-gelatinized starch is 8:1 to 1:1, the ratio between water and the total amount of the unpre-gelatinized starch and the pre-gelatinized starch is 0.2:1 to 0.7:1, and the biocide in *Bacillus thuringiensis;*
    (b) drying said mass by heating said mass at temperatures between 50° and 100° C. for no more than 30 minutes to form a dried mass; and
    (c) crushing the dried mass to form said biocidal formulation.

2. The method for the preparation of a biocidal formulation according to claim 1 wherein the ratio between the unpre-gelatinized starch and the pre-gelatinized starch is 5:1 to 3:1.

3. The method for the preparation of a biocidal formulation according to claim 1 wherein the ratio between water and the total amount of the unpre-gelatinized starch and the pre-gelatinized starch is 0.25:1 to 0.55:1.

4. The method for the preparation of a biocidal formulation according to claim 1 wherein the step of drying is conducted at temperatures between 60° and 90° C.

5. The method for the preparation of a biocidal formulation according to claim 1 wherein the step of drying takes between 3 and 15 minutes.

* * * * *